(12) United States Patent
Penner

(10) Patent No.: US 10,415,034 B2
(45) Date of Patent: Sep. 17, 2019

(54) METHOD FOR THE SELECTION OF APTAMERS FOR UNBOUND TARGETS

(71) Applicant: NEOVENTURES BIOTECHNOLOGY INC., Ontario (CA)

(72) Inventor: Gregory Penner, Ontario (CA)

(73) Assignee: NEOVENTURES BIOTECHNOLOGY INC., Ontario (CA)

( * ) Notice: Subject to any disclaimer, the term of this patent is extended or adjusted under 35 U.S.C. 154(b) by 5 days.

(21) Appl. No.: 15/757,536

(22) PCT Filed: Sep. 2, 2016

(86) PCT No.: PCT/CA2016/051048
§ 371 (c)(1),
(2) Date: Mar. 5, 2018

(87) PCT Pub. No.: WO2017/035666
PCT Pub. Date: Mar. 9, 2017

(65) Prior Publication Data
US 2019/0112593 A1    Apr. 18, 2019

Related U.S. Application Data

(60) Provisional application No. 62/214,564, filed on Sep. 4, 2015.

(51) Int. Cl.
*C12N 15/10* (2006.01)
*C12N 15/115* (2010.01)

(52) U.S. Cl.
CPC .................. *C12N 15/1048* (2013.01)

(58) Field of Classification Search
None
See application file for complete search history.

(56) References Cited

U.S. PATENT DOCUMENTS 5,475,096 A    12/1995    Gold et al.
5,631,146 A    5/1997    Szostak et al.
7,745,607 B2    6/2010    Li et al.

OTHER PUBLICATIONS

Mendonsa et al., In Vitro Evolution of Functional DNA Using Capillary Electrophoresis, Journal of the American Chemical Society, 2004, pp. 20-21, vol. 126, No. 1.
Neoventures Biotechnology Inc, "Newsletter #7: Aptamer free/free selection", Technical bulletin, Sep. 16, 2015, pp. 1-2, online, retrieved on Oct. 31, 2016, Retrieved from Internet: <http://neoventures.ca/wp-content/uploads/2015/09/Newsletter-4-Freelex-a-new-aptamer-discovery-plafform.pdf>.
International Search Report, dated Nov. 10, 2016, from corresponding PCT application No. PCT/CA2016/051048.

*Primary Examiner* — Tracy Vivlemore
(74) *Attorney, Agent, or Firm* — Young & Thompson

(57) ABSTRACT

Disclosed is a method for the selection of aptamers that does not require immobilization of the target or the oligonucleotide library. The method includes: (i) combining a selection library of oligonucleotides that contain a random region flanked by primer recognition sites with blocker oligonucleotides that anneal to the primer recognition sites; (ii) exposing the blocked selection library to an immobilization field including random oligonucleotides and removing unbound selection library oligonucleotides; (iii) recovering the selection library oligonucleotides that bound to the immobilization field and combining with a target analyte of interest; (iv) exposing the selection library oligonucleotides-target analyte mixture to an immobilization field; and (v) recovering those selection library oligonucleotides that did not bind to the immobilization field.

12 Claims, 1 Drawing Sheet
Specification includes a Sequence Listing.

SEQUENCE LISTING

```
<160> NUMBER OF SEQ ID NOS: 23

<210> SEQ ID NO 1
<211> LENGTH: 23
<212> TYPE: DNA
<213> ORGANISM: Artificial Sequence
<220> FEATURE:
<223> OTHER INFORMATION: Blocker

<400> SEQUENCE: 1
atcatatgtc cttctcttcc cta                                            23

<210> SEQ ID NO 2
<211> LENGTH: 23
<212> TYPE: DNA
<213> ORGANISM: Artificial Sequence
<220> FEATURE:
<223> OTHER INFORMATION: Blocker

<400> SEQUENCE: 2
tcaagtggtc atgtactagt caa                                            23

<210> SEQ ID NO 3
<211> LENGTH: 40
<212> TYPE: DNA
<213> ORGANISM: Artificial Sequence
<220> FEATURE:
<223> OTHER INFORMATION: Aptamer

<400> SEQUENCE: 3
tagagaaggc aagaaaaagt gaaagagaag tgaaccgagt                          40

<210> SEQ ID NO 4
<211> LENGTH: 40
<212> TYPE: DNA
<213> ORGANISM: Artificial Sequence
<220> FEATURE:
<223> OTHER INFORMATION: Aptamer

<400> SEQUENCE: 4
aaacaggtaa gataaaggta gtgagtacca ggacgcaagg                          40

<210> SEQ ID NO 5
<211> LENGTH: 40
<212> TYPE: DNA
<213> ORGANISM: Artificial Sequence
<220> FEATURE:
<223> OTHER INFORMATION: Aptamer
```

<400> SEQUENCE: 5
gattcgatct ggataaagtg gagtgactgt gtatgtgtga                    40

<210> SEQ ID NO 6
<211> LENGTH: 40
<212> TYPE: DNA
<213> ORGANISM: Artificial Sequence
<220> FEATURE:
<223> OTHER INFORMATION: Aptamer

<400> SEQUENCE: 6
caaaactaac gaatcacgat gcgctctgcg tagtctgagc                    40

<210> SEQ ID NO 7
<211> LENGTH: 40
<212> TYPE: DNA
<213> ORGANISM: Artificial Sequence
<220> FEATURE:
<223> OTHER INFORMATION: Aptamer

<400> SEQUENCE: 7
tagttcgagt aaacgagcca agagctaaat agcaaatgaa                    40

<210> SEQ ID NO 8
<211> LENGTH: 40
<212> TYPE: DNA
<213> ORGANISM: Artificial Sequence
<220> FEATURE:
<223> OTHER INFORMATION: Aptamer

<400> SEQUENCE: 8
tgaagataaa aagcccataa acaactattg gtacgagatc                    40

<210> SEQ ID NO 9
<211> LENGTH: 40
<212> TYPE: DNA
<213> ORGANISM: Artificial Sequence
<220> FEATURE:
<223> OTHER INFORMATION: Aptamer

<400> SEQUENCE: 9
acgggataat taactagaca gtatcacgtt tggctattag                    40

<210> SEQ ID NO 10
<211> LENGTH: 40
<212> TYPE: DNA
<213> ORGANISM: Artificial Sequence
<220> FEATURE:
<223> OTHER INFORMATION: Aptamer

<400> SEQUENCE: 10
agtcaatcac ttcacttacg tggttatctg tttgataagc                    40

<210> SEQ ID NO 11
<211> LENGTH: 40
<212> TYPE: DNA
<213> ORGANISM: Artificial Sequence
<220> FEATURE:
<223> OTHER INFORMATION: Aptamer

<400> SEQUENCE: 11
aaacaagagg acatcgtgac aaacgatata aatgtgattg                    40

<210> SEQ ID NO 12

```
<211> LENGTH: 40
<212> TYPE: DNA
<213> ORGANISM: Artificial Sequence
<220> FEATURE:
<223> OTHER INFORMATION: Aptamer

<400> SEQUENCE: 12
aagtcgtatg tctaaaacaa gactgtaatg cacctcatct                40

<210> SEQ ID NO 13
<211> LENGTH: 40
<212> TYPE: DNA
<213> ORGANISM: Artificial Sequence
<220> FEATURE:
<223> OTHER INFORMATION: Aptamer

<400> SEQUENCE: 13
gatgggtaca agcaaggcag gccagttcta ttaaagtgtg                40

<210> SEQ ID NO 14
<211> LENGTH: 40
<212> TYPE: DNA
<213> ORGANISM: Artificial Sequence
<220> FEATURE:
<223> OTHER INFORMATION: Aptamer

<400> SEQUENCE: 14
aagaggataa aaacggctga gcttggcagt cacatatgaa                40

<210> SEQ ID NO 15
<211> LENGTH: 40
<212> TYPE: DNA
<213> ORGANISM: Artificial Sequence
<220> FEATURE:
<223> OTHER INFORMATION: Aptamer

<400> SEQUENCE: 15
gtagaccacc gcacgaccgc tgatgctctt tggctgtcga                40

<210> SEQ ID NO 16
<211> LENGTH: 40
<212> TYPE: DNA
<213> ORGANISM: Artificial Sequence
<220> FEATURE:
<223> OTHER INFORMATION: Aptamer

<400> SEQUENCE: 16
taatggcgta cacgcctacg acaccaaaac ttcacttttg                40

<210> SEQ ID NO 17
<211> LENGTH: 40
<212> TYPE: DNA
<213> ORGANISM: Artificial Sequence
<220> FEATURE:
<223> OTHER INFORMATION: Aptamer

<400> SEQUENCE: 17
ttgaaaagaa gatggacggt taagtgtaga cctggaatat                40

<210> SEQ ID NO 18
<211> LENGTH: 40
<212> TYPE: DNA
<213> ORGANISM: Artificial Sequence
<220> FEATURE:
<223> OTHER INFORMATION: Aptamer

<400> SEQUENCE: 18
```

```
tggaatcaaa tggctctcgc ccgacacaag tgaatgccat                          40

<210> SEQ ID NO 19
<211> LENGTH: 40
<212> TYPE: DNA
<213> ORGANISM: Artificial Sequence
<220> FEATURE:
<223> OTHER INFORMATION: Aptamer

<400> SEQUENCE: 19
ctaaggttga aataataagc ggtcagataa agtgagggta                          40

<210> SEQ ID NO 20
<211> LENGTH: 40
<212> TYPE: DNA
<213> ORGANISM: Artificial Sequence
<220> FEATURE:
<223> OTHER INFORMATION: Aptamer

<400> SEQUENCE: 20
atagaagacg ttcgacgtat gttaacaggg ggaaggaaag                          40

<210> SEQ ID NO 21
<211> LENGTH: 40
<212> TYPE: DNA
<213> ORGANISM: Artificial Sequence
<220> FEATURE:
<223> OTHER INFORMATION: Aptamer

<400> SEQUENCE: 21
ctatgactta ttattgggag taggaatgag ctacattacc                          40

<210> SEQ ID NO 22
<211> LENGTH: 40
<212> TYPE: DNA
<213> ORGANISM: Artificial Sequence
<220> FEATURE:
<223> OTHER INFORMATION: Aptamer

<400> SEQUENCE: 22
acataaaaaa gagatgcgtg taatggagac ataaaaccaa                          40

<210> SEQ ID NO 23
<211> LENGTH: 40
<212> TYPE: DNA
<213> ORGANISM: Artificial Sequence
<220> FEATURE:
<223> OTHER INFORMATION: Aptamer

<400> SEQUENCE: 23
ggatcaaggg aaaggacaag tagacctaag cgtttgaaat                          40
```

METHOD FOR THE SELECTION OF APTAMERS FOR UNBOUND TARGETS

FIELD OF THE INVENTION

The present invention relates to the selection of aptamers. In particular, it relates to methods for the selection of aptamers using unbound target baits.

BACKGROUND OF THE INVENTION

Aptamers are oligonucleotides that mimic antibodies in their ability to act as ligands and bind to analytes. U.S. Pat. No. 5,475,096 teaches a method for the in vitro selection of DNA or RNA molecules that are capable of binding specifically to a target molecule. This patent discloses a method of reiterative selection of oligonucleotides that has come to be known as "Systematic Evolution of Ligands by Exponential Enrichment" or SELEX. Within such a method, there is a need to separate those oligonucleotide sequences that have bound to the target from those that have not. All methods employing SELEX require a process for partitioning oligonucleotide sequences that have bound to the analyte of interest from oligonucleotide sequences that have not bound to the analyte of interest. In U.S. Pat. No. 5,475,096, this partitioning process is taught as the use of nitrocellulose membranes. Single stranded oligonucleotides will pass through nitrocellulose while many analyte molecules, in particular protein analytes, will not. Oligonucleotides that are not bound to the analyte will therefore pass through nitrocellulose, whereas oligonucleotides that are bound to the analyte will not pass through and thus can be partitioned from those that do.

The use of nitrocellulose as a means of partitioning oligonucleotides that have bound to a target analyte from oligonucleotides that have not bound to the target analyte is limited in use to those analytes that will not readily pass through nitrocellulose. This means that this is not an appropriate method for the selection of aptamers for small molecules, including but not limited to such examples as metabolites, drugs, antibiotics, peptides, and toxins, or any molecule that will pass through nitrocellulose.

In practice, we have also found difficulties with the use of this method as many proteins may pass through nitrocellulose to a certain extent.

In practice, we have also found that this method can include selection for oligonucleotide sequences that are capable of strong secondary structure and thus do not pass through nitrocellulose even though they do not bind to the target analyte. The selection of such sequences is undesirable.

U.S. Pat. No. 5,475,096 also suggests that partitioning of oligonucleotides that are bound to a target analyte from oligonucleotides that are not bound to a target analyte can also be achieved by immobilizing the target analyte within a column. This is a very common method and has been used successfully in a wide variety of applications.

The immobilization of a target analyte within a column does suffer from certain drawbacks however. One significant constraint is in regard to small molecules. The conjugation of the small molecule to a solid support in order to effect immobilization not only changes the chemical group on the small molecule used for conjugation, but also has the potential to change the entire electron charge cloud and resonance characteristics of the analyte. In such instances, it is possible to select an aptamer that binds well to the immobilized target analyte but not to the free form of the analyte. This is undesirable for diagnostic purposes when the knowledge of the quantity of the free analyte is being sought.

The immobilization of a target analyte within a column also renders it difficult to perform selection for complexes among molecules. It is an important aspect of these procedures to remove non-immobilized target from the solid support with washes. If this is not performed, then oligonucleotides may bind to a target that is subsequently lost in a wash step. This washing of the column to remove non-immobilized targets also removes any molecules that may be bound to the immobilized target in a non-covalent manner. Such complexes can be potentially rebuilt if the nature of these complexes is known. If the nature of the complex is not known however, then the complexes cannot be rebuilt.

An important part of the selection process is the washing of the bound oligonucleotides in order to increase stringency of the selection process. Weakly bound complexes will be disrupted by such washes, or may be disrupted by wash steps implicit in the conjugation process itself. Thus, this is not a sufficiently reliable method for the selection of molecular complexes.

An epitope can be defined as the region on an analyte that a ligand interacts with in terms of binding. An epitope can be a contiguous stretch within the target analyte or can be represented by multiple points that are physically proximal in a folded form of the target analyte. The immobilization of a target analyte within a column necessarily disrupts at least one epitope within the target molecule. The nature of the epitope disruption is a function of the conjugation process used. For example, conjugation relying on thiol groups on proteins will disrupt epitopes within the protein that involve cysteine residues. Such a conjugation has the potential to disrupt not only the epitope involving the residue conjugated, but also, may affect protein folding on a more global level and affect other non-proximal epitopes. This is undesirable as aptamers may be selected upon their binding to the immobilized target analyte but not to the free target analyte.

It is often desirable to obtain ligands for multiple epitopes within a target analyte. This enables the use of multiple ligands simultaneously to either capture or detect the target analyte in a diagnostic device. The removal of at least one epitope from selection is undesirable as this reduces the number of epitopes that ligands are selected for.

Mendonsa S. D. and Bowser M. T., *In vitro evolution of functional DNA using capillary electrophoresis.* 2004 Jan. 14. *J Am. Chem. Soc.* 126(1):20-1 provides a description of the use of capillary electrophoresis for the selection of aptamers against target analytes. This method does not require immobilization of either target analyte or oligonucleotides as partitioning is based on the different flow properties of the oligonucleotides bound to the target analyte as compared to both the unbound oligonucleotides and the unbound target analyte.

The method of capillary electrophoresis represents a step forward from approaches based on immobilization but still faces significant constraints. The method is not conducive for use with small molecules, as small molecules will not shift the flow of the bound oligonucleotides sufficiently from the unbound oligonucleotides.

The method of capillary electrophoresis may cause complexes among proteins or between proteins and metabolites to be disrupted by the forces of the electrical fields involved in the separation and/or the flow of the solutions. Thus, this is not a desirable selection platform for complexes.

Moreover, the method of capillary electrophoresis cannot be readily applied to complex mixtures such as blood serum, cerebral spinal fluid, urine, sweat, saliva, menstrual fluid, fecal suspensions, cell or tissue suspensions, or plant phloem solution as the identification of the bound oligonucleotides will not be possible given the complexity of the matrix.

Several other methods are known in the art such as flow cytometry, magnetic capillary electrophoresis, gel filtration, density gradient separation, and surface plasmon resonance. Each of these methods suffer from at least one of the constraints listed above.

U.S. Pat. No. 5,631,146 teaches how to use affinity chromatography to select a single stranded DNA molecule (oligonucleotide) that is capable of binding specifically to adenosine molecules.

U.S. Pat. No. 7,745,607 claims a method for the selection of aptamers which involves the use of sense and antisense pairing. Aptamer selection invariably involves the synthesis of libraries of oligonucleotides that contain known primer sequences on either end flanking a random region. U.S. Pat. No. 7,745,607 exploits this by introducing an antisense sequence for one of the known sequences flanking the random region.

The present invention is substantially different. It relies on antisense binding to the random region. This is important because it is the random region that binds to the target molecule. For U.S. Pat. No. 7,745,607 to work, there must be either an interaction between the random region and the known sense sequence, or a translational conformation shift that affects the ability of the known sense sequence capacity to bind to an antisense. In the present invention, this is not required. In the present invention, we are selecting directly for conformational changes in the random region only. This represents a larger proportion of potentially binding sequences than could be detected through the use of U.S. Pat. No. 7,745,607. This means that with the present invention, it is possible to identify more aptamers from a selection process that bind to the target molecule. The ability to select more aptamers implicitly means, on a probability basis, that it is possible to select better aptamers.

The present invention also involves selection against shapes that are not capable of binding to the immobilized antisense oligonucleotides. This reduces the potential for selection of sequence shapes that are favored by the selection process to form shapes that do not bind to the antisense sequence in the absence of any target to bind to. This can be a very significant problem for selection and is not prevented in any way by U.S. Pat. No. 7,745,607. The present invention effectively eliminates this as an issue. This means that the present invention will not mistakenly select for sequences that form certain structures in the absence of the target.

The present invention represents thus an improvement over all of these other approaches as it enables the following:
No need for immobilization of either oligonucleotide sequences or target analytes in the selection process;
Generic application to all targets regardless of size;
Capacity to modulate stringency;
Direct selection for binding with the random nucleotide region of the aptamer;
Direct selection for a shift in the shape of the aptamer;
Selection against sequences that would not bind to an antisense sequence in the absence of the target analyte.

This invention enables several new approaches to aptamer selection that were not possible previously. Certain of these are listed below. This list is meant to be illustrative of the nature of new approaches enabled by this approach and is not meant to be exhaustive.

The ability to perform completely free/free selection enables selection for target analytes in complex mixtures such as blood serum, cerebrospinal fluid, urine, sweat, saliva, menstrual fluid, fecal suspensions, cell lysate suspensions, plant phloem fluid, ground water.
The ability to select aptamers for complexes for example including but not limited to complexes formed between proteins, or between proteins and metabolites, or between metabolites, without a risk that the immobilization process or the selection process may disrupt the complex.
The ability to select for small molecules without affecting their structure or binding capacity through conjugation.

SUMMARY

The present invention relates to a method for the selection of aptamers, which comprises the following steps:
a) combining a library of oligonucleotides that contain a random region flanked by two primer recognition sites (selection library) with blocker oligonucleotides (blockers) that anneal to the primer recognition sites to obtain a blocked selection library;
b) exposing the blocked selection library to an immobilization field comprising immobilized oligonucleotides;
c) removing sequences from the blocked selection library that are not bound to the immobilization field;
d) recovering blocked selection library that were bound to the immobilization field;
e) combining and incubating these recovered blocked selection library sequences with a target analyte;
f) exposing the mixture of step e) with an immobilization field as in step b);
g) retaining those blocked selection library sequences that do not bind to the immobilization field;
h) exposing the retained blocked selection library sequences to PCR amplification;
i) repeating steps a) to h) to achieve the level of selection desired.

In one embodiment, the blocked selection library is incubated with a counter-selection target analyte or complex of analytes prior to the first exposure of step b) described here above.

In one embodiment, the target analyte and/or the counter-selection target analyte is/are metabolites, toxins, proteins, peptides, cell wall or cell membrane constituents, living or dead tissue and/or complexes among any of these individual elements either as pairs or in more multitudinous combinations.

In one embodiment, the target analyte and/or the counter-selection target analyte is/are either known or unknown but is/are present within a pre-existing complex mixture.

In one embodiment, the target analyte is either known or unknown but is present within a pre-existing complex mixture and a pre-existing complex mixture is used as a counter-selection target analyte.

In one embodiment, the target analyte is a complex formed between molecules.

In another embodiment, the target analytes may be complexes formed between molecules.

In one embodiment, the oligonucleotides useful in this method are composed solely of natural DNA nucleotides, natural RNA nucleotides, modified DNA nucleotides or modified RNA nucleotides.

In another embodiment, the oligonucleotides useful in this method are a combination of any one of natural DNA nucleotides, natural RNA nucleotides, modified DNA nucleotides and/or modified RNA nucleotides.

In one embodiment, the immobilization field oligonucleotides are composed solely of natural DNA nucleotides, natural RNA nucleotides, modified DNA nucleotides or modified RNA nucleotides.

In another embodiment, the immobilization field oligonucleotides useful in this method are a combination of any one of natural DNA nucleotides, natural RNA nucleotides, modified DNA nucleotides and/or modified RNA nucleotides.

In one embodiment, the selection library oligonucleotides are composed solely of natural DNA nucleotides, natural RNA nucleotides, modified DNA nucleotides or modified RNA nucleotides.

In another embodiment, the selection library oligonucleotides useful in this method are a combination of any one of natural DNA nucleotides, natural RNA nucleotides, modified DNA nucleotides and/or modified RNA nucleotides.

In one embodiment, the blocker oligonucleotides useful in this method are composed solely of natural DNA nucleotides, natural RNA nucleotides, modified DNA nucleotides or modified RNA nucleotides.

In another embodiment, the blocker oligonucleotides useful in this method are a combination of any one of natural DNA nucleotides, natural RNA nucleotides, modified DNA nucleotides and/or modified RNA nucleotides.

In one embodiment, the oligonucleotides within the immobilization field have a length of 8 nucleotides.

In a preferred embodiment, the oligonucleotides within the immobilization field are further extended to nine or ten nucleotides at a later stage in later selection rounds, to increase the stringency of selection.

In one embodiment, stringency of selection is increased by applying two positive selections.

DETAILED DESCRIPTION OF THE INVENTION

As used herein, the term "about" preceding a figure means plus or less 10% of the value of said figure.

The invention is composed of the following components:

1. Immobilization field: this is composed of random antisense oligonucleotides immobilized onto a surface. The length of the antisense oligonucleotides can vary and may even be constituted of mixed lengths. The randomness of the immobilization field represents one embodiment of the invention. It is imaginable that given sufficient knowledge of sequences that have capacity to bind to such a field, the randomness of the field could be reduced.

2. Selection library: this is generally similar to that described throughout the literature in SELEX selection strategies. A preferred embodiment consists of two known primer recognition sequences flanking an unknown random region of variable length.

The length of the primer recognition sequences is a function of their sequence and thus, their annealing temperature. A preferred embodiment are primer recognition sequences that have an annealing temperature higher than 60° C., and less than 72° C. In the design of primer recognition sequences and hence, the design of the primers, care should be taken to minimize potential for annealing among sequences, fold back regions within sequences, or annealing of the same sequence itself.

A preferred embodiment are primer recognition sequences between about 10 to 40 nucleotides, preferably between about 12 to 30 nucleotides, more preferably between about 18 to 26 nucleotides, i.e., about 18, 19, 20, 21, 22, 23, 24, 25 or 26 nucleotides.

The length of the variable region of the selection library is not material to the enablement of this invention. A preferred embodiment is a random region between 10 and 100 nucleotides, preferably between about 20 and 60 nucleotides, more preferably about 40 nucleotides.

Random regions shorter than this may be used but may be constrained in their ability to form secondary or tertiary structures and thus constrained in their ability to bind to target molecules.

Random regions longer than this may also be used but may present difficulties in terms of cost of synthesis.

The randomness of the variable region is also not a constraint to this invention. Spiked sequence selection libraries may work as well or better than completely random ones, given that some knowledge exists regarding sequences or the nature of sequences that bind to a given target.

3. Blockers: these are antisense elements created to anneal to the known primer regions on the selection library. A preferred embodiment is that the blocker sequence has at least 70%, preferably at least 80%, more preferably at least 90%, even more preferably 100% homology with the primer recognition sequence so as to avoid potential for binding of the blocker sequences to the random region. They do not necessarily have to have complete homology or even bind to the entire known primer sequence for the enablement of this invention.

4. Target: this is any molecular target, including metabolites, toxins, proteins, peptides, cell wall or cell membrane constituents, living or dead tissue and/or complexes among any of these individual elements either as pairs or in more multitudinous combinations.

5. Antisense library: this is produced after the first round of selection and is used in subsequent rounds for selection as well. This is not a necessary enablement of this invention. The antisense library may be completely eliminated from the library after amplification and before selection without materially affecting the invention. This may or may not improve the selection process.

An immobilization field is prepared by synthesizing oligonucleotides with a chemical moiety suitable for use in attachment of the oligonucleotides to a surface.

Such chemical moieties may include but are not limited to disulphide, thiol, amine, methacryl, digoxigenin, biotin, I-linker, adenyl, or hexynyl groups on either the 5' or 3' end of an oligonucleotide to be immobilized.

Surfaces used to enable this invention may include, but are not limited to, gold, dextran, streptavidin, or other functionalized group surfaces.

One embodiment of this invention is the use of oligonucleotides composed solely of or being a combination of any one of natural DNA nucleotides, natural RNA nucleotides, modified DNA nucleotides and/or modified RNA nucleotides.

One enablement of this invention is the use of oligonucleotides with a length of about 6 to 12 nucleotides, preferably about 8 nucleotides, which are immobilized onto a gold surface through interaction with a disulphide group on the 5' end of each oligonucleotide. Several considerations should be taken into account when choosing an appropriate oligonucleotide length for use in the immobilization field.

One consideration is the potential for bias in the immobilization field if the number of possible sequences in the immobilized oligonucleotides is a larger amount than the amount of sequences that can be immobilized within the surface area used. The number of possible sequences of any given oligonucleotide length is provided by the formula $4^L$ [4 to the power of L], wherein L corresponds to the number of nucleotides in the sequence. A sequence length of 8 corresponds to a total of 65,536 sequences. This is an amount that would assure that each sequence is represented multiple times when immobilized on a surface area less than a $cm^2$.

Another consideration for the length of the oligonucleotides being immobilized within the immobilization field is the binding strength of such sequences with the random region of the selection library. The length of the oligonucleotides should be sufficient so that they are capable of binding to homologous sequences at the temperature at which the selection process will occur. An eight nucleotide sequence composed entirely of A's or T's has a predicted melting temperature for its homologous sequence of 19.8° C. This represents one of the weakest binding sequences and still a significant proportion of such sequences will anneal at a room temperature of 20° C.

Another consideration for the length of the oligonucleotide being immobilized within the immobilization field is that the binding affinity of such sequences within the random region of the selection library is not stronger (i.e., has a lower kD value) than that of the prospective target for the aptamer. In most cases, the potential binding affinity of the target for an aptamer is not known precisely prior to the selection process but an expected range can be defined. An eight nucleotide sequence composed entirely of C's or G's has a predicted melting temperature for its homologous sequence of 53.2° C. Clearly, this sequence will bind more tightly to a homologous sequence than an A or T rich sequence, which would have a much lower melting temperature.

A summary of the last two considerations is that the length of the oligonucleotides being immobilized within the immobilization field should represent sequences that at a minimum are able to bind to homologous sequences at room temperature, and should minimize the inclusion of sequences that bind more tightly than is necessary for selection to proceed effectively. It is suggested that an oligonucleotide library comprising oligonucleotides with a length of about 6 to 12 nucleotides, preferably about 8 nucleotides would serve as a preferred enablement of this invention.

It is contemplated by the inventors that one means of increasing stringency through the selection process would be to use progressively longer oligonucleotides in the immobilization field. Thus, in one embodiment, initial rounds of selection are carried out using oligonucleotides with a length of about 6 to 12 nucleotides, preferably about 8 nucleotides; while later rounds of selection are carried out using oligonucleotides which are longer than those in the initial rounds, i.e., oligonucleotides with a length of about 8, 9, 10, 11, 12 nucleotides, preferably about 9 or 10 nucleotides.

The selection library is composed of natural or synthetic oligonucleotides.

In one embodiment, these oligonucleotides are composed solely of or are a combination of any one of natural DNA nucleotides, natural RNA nucleotides, modified DNA nucleotides and modified RNA nucleotides.

In one embodiment, these oligonucleotides may contain a random region of any length.

One enablement of this invention includes a random region that is between 10 and 100 nucleotides in length, preferably between about 20 and 60 nucleotides in length, more preferably about 40 nucleotides in length.

The blockers used as an enablement of this invention have at least 70%, preferably at least 80%, more preferably at least 90%, even more preferably 100% homology, i.e., complete homology with the primer recognition sequences. Complete homology may however not be necessary as an enablement of this invention but would seem to be desirable in order to effectively block the ability of the primer recognition sequences to affect the selection process.

The purpose of the blockers is to prevent both the primer recognition sites within the selection library from folding back and interacting with the random region. The purpose of the blockers is also to prevent the immobilization field from binding to the primer recognition sites. Effectively, the use of the blockers focuses the selection process on the random region of the selection library.

For a schematic diagram of the random library and blockers, see FIG. 1.

Targets may be anything that can be dissolved or effectively suspended in solution. For the purposes of this invention, the concept of target(s) is not limited to a predefined molecular entity. The target(s) may be unknown prior to selection. It this case, the target(s) is/are present within a pre-existing complex mixture.

A concept enabled by this invention is the use of several targets to increase stringency, i.e., the use of at least 2, 3, 4, 5 or more different targets in subsequent selection rounds.

Another concept enabled by this invention is the use of complex mixtures from samples that are derived from individuals that are all exhibiting the same phenotype. Complex mixtures include, but are not limited to, blood serum, cerebrospinal fluid, urine, sweat, saliva, menstrual fluid, fecal suspensions, cell lysate suspensions, plant phloem fluid, and ground water. An example could be blood serum from individuals who have been diagnosed with type II diabetes. In this case, the number of target analytes cannot be quantified and is thus illimited.

This invention allows and supports the use of counter-selection as a means of selecting for specificity with the aptamers for the target analytes. As such, the range of counter-selection target analytes used is as broad as the range of target analytes used.

Counter-selection is a process whereby oligonucleotides are discarded from a selected library on the basis of their ability to bind to a counter-selection target analyte. With defined targets, the counter-selection target analyte is generally a molecule or protein that is similar to the positive target analyte but represents a target analyte that we are not interested in measuring.

In one embodiment, several counter-selection target analytes are used for counter-selection, i.e., at least 2, 3, 4, 5 or more counter-selection target analytes.

In a complex mixture, the counter-selection target analytes are generally those elements that would be held in common across complex mixtures, such as those elements held in common between blood serum from healthy individuals and blood serum from individuals that exhibited a certain pathology. In this case, the number of counter-selection target analytes cannot be quantified and is thus illimited.

The fifth component of this invention is the antisense library. It is synthesized through PCR amplification of the selection library after the first selection round. In an enablement of the present invention, the antisense library was not removed from the selection process. The double stranded selection library was exposed after PCR amplification to denaturation, followed by rapid cooling in ice. This favors the formation of folded structures of either strand, over annealing and subsequent double strand formation.

Another consideration for the retention of the antisense library is as another effective means for blocking the primer recognition sites from interfering with the selection process. Blocker oligonucleotides are added to the selection library and the antisense library in all relevant senses, such that the primer recognition sites on the selection library and on the antisense library are all blocked. However, the complexity of the library will stay quite high even after several rounds of selection. The probability that the random region of a sense sequence will find its perfect homolog in the antisense library is very small given that annealing will be driven by the homologous primer recognition sequences that all antisense and sense sequences have. This drive a phenomenon that the inventor has described publicly as "dubbles". A dubble is an oligonucleotide that is double stranded on both ends and these ends are connected by weakly or non-annealed single stranded sequences. The retention of the antisense sequences in the selection process will create dubbles and will, as such, provide further protection against the primer recognition sequences interfering with the selection process.

An advantage to retaining the antisense sequences in the selection process is that this provides more sequences and hence more potential ligands to participate. A larger solution space has the potential to lead to better solutions.

The present invention will be further understood from the following examples. However, the scope of protection of the present invention shall not be limited to these examples.

EXAMPLES

Figure 1:
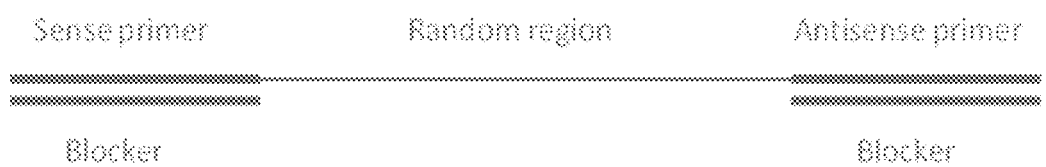
FIG. 1 is a schematic diagram of the random library and blockers used as an enablement of this invention.

Material and Methods
Preparation of the Immobilization Field

The immobilization field was prepared by synthesizing a random library of eight nucleotide oligonucleotides with a disulphide group on the 5' end (immobilization field library). The library was dissolved at a concentration of 10 µM in a 1× PBS buffer. The surface of a gold coated glass slide with dimensions of 9 mm square was used. This surface was treated with five sequential 10 µL drops of the immobilization field library. The slide was then allowed to dry for 1 hour in the dark in order to facilitate conjugation of the immobilization field library onto the gold surface.

After this incubation period, the immobilization field library is considered to have been conjugated onto the gold surface. The remaining solution is removed, and the surface is allowed to dry at room temperature.

The remaining surface is then blocked with short PEG molecules having the following formula: $CH_3O-(CH_2CH_2O)_n-CH_2CH_2SH$ and an average molecular weight of 550 daltons. The PEG molecules are applied at a concentration of 286 µM in 1× PBS buffer and allowed to incubate overnight, prior to removal. This process is repeated in a second blocking step, with an incubation period of 30 minutes at room temperature.

Following blocking of the chip, the latter is washed in 1× selection buffer (10 mM HEPES, pH 7.4, 120 mM NaCl, 5 mM KCl, 5 mM $MgCl_2$) for 5 minutes with shaking at room temperature. This comprises a general description of the preparation of the immobilization field.

Shape Selection Phase

An aliquot of the selection library comprising about $10^{15}$ sequences is diluted in 1× selection buffer in a total volume of 50 µL. An equimolar amount of each of the sense blocker sequences (SEQ ID NOs: 1-2) was incubated with the selection library in a total volume of 100 µL. This solution was heated for 10 minutes at 95° C. to ensure removal of any secondary or tertiary structures which could interfere with the proper annealing of the blockers to the selection library. The blockers were then allowed to anneal to the selection library by allowing the mixture to equilibrate to room temperature for 30 minutes.

This blocked selection library is then exposed to the immobilization field in five sequential 10 µL drops for the "Shape Selection Phase" of selection. The blocked selection library is incubated on the immobilization field for 30 minutes with slow shaking in an incubator at room temperature. The solution remaining on top after this time period is removed and discarded. The chip is washed with the addition of 50 µL of TE buffer (10 mM Tris, pH 8.0, 1 mM EDTA). After incubation at room temperature for two minutes, the buffer is discarded. Optionnaly, this wash step can be repeated once, twice, three times, four times or five times. Ideally, this wash step is repeated just once or twice, but not more than three to five times.

We have found that the EDTA component in TE buffer chelates magnesium ions, and aids in the elution of oligo sequences bound to the immobilization field.

The blocked selection library sequences which were bound to the immobilization field are recovered from the chip by immersing the chip in 1 mL of selection buffer in a 1.5 mL plastic tube and heating to 95° C. for fifteen minutes. The solution is removed to a fresh tube before cooling, and the process is repeated with the addition of fresh 1 mL selection buffer in a fresh tube. The two elution solutions (2 mL in total) are combined. The first selection round selected library is re-annealed with the blockers, by cooling the solutions to room temperature for 15 minutes prior to passing the entire 2 mL through a PCR clean up column (Thermo Scientific GeneJET PCR Purification Kit), following manufacturer's instructions. The purified blocked selection library is eluted with 30 µL of water.

Target Selection Phase

The target molecule is then added to this purified blocked selection library solution in an appropriate concentration of selection buffer to bring the total volume to 50 µL. This solution is added to an immobilization field in five sequential 10 µL drops and incubated for 30 minutes with shaking in an incubator at room temperature. This represents the "Target Selection Phase" of each selection round.

The remaining solution, i.e., the purified blocked selection library sequences that did not bind to the immobilization field in presence of the target molecule, is carefully collected with a pipet tip, and saved to a fresh tube. This solution is subjected to PCR cleanup as described for the "Shape Selection Phase", however, instead of eluting from the PCR cleanup column with 30 µL of water, elution is carried out from the PCR cleanup column with 400 µL of water at this stage. The recovered purified library is subjected to PCR amplification in a two-step process. First, we perform test PCR reactions by performing different numbers of sequential PCR cycles on 5µL samples of the library template. The products of each of these PCR reactions are analyzed by gel electrophoresis (10% acrylamide gels, with ethidium bromide staining) to determine the optimum number of cycles required for amplification. By optimum, we mean as high a yield as possible without the appearance of any concatemers of the PCR product. Then, this number of PCR cycles is applied to 5μL aliquots of the library for amplification.

The combination of "Shape Selection Phase" and "Target Selection Phase" corresponds to a selection round. The inclusion of the "Shape Selection Phase" in each selection round is however optional, but including this phase in the first round or first few rounds of selection is a preferred embodiment of this invention.

In one embodiment, as many selection rounds as needed are carried out to achieve the level of selection desired.

In a preferred embodiment, between about 1 and 20 selection rounds are carried out, preferably between about 3 and 15, more preferably between about 6 and 12.

In one embodiment, a multiple-positive selection is carried out, i.e., several different target analytes are used in subsequent rounds, to increase stringency of selection.

In a preferred embodiment, two positive selections are carried out, i.e., two different target analytes are used in subsequent rounds, to increase stringency of selection.

According to the above embodiments, two or more target analytes can be used during the Target Selection Phase either alternatively at each round of selection, or alternatively after several rounds, i.e., at each about 2, 3, 4, 5, 6 or more rounds of selection.

Counter selection, if carried-out, is performed by including the counter selection target(s) in the "Shape Selection Phase". In this way, sequences that may have shapes that bind to the immobilization field but do not do so because they are bound to the counter selection agent(s), are selected against.

In a preferred embodiment, the counter-selection step is carried out during the "Shape Selection Phase", before exposing the blocked selection library to the immobilization field.

Example 1

24(S) Cholesterol

The method according to the present invention was applied for the selection of aptamers binding to the molecule 24(S) cholesterol (CAS number 474-73-7).

Selection was performed for 10 selection rounds, using a completely random selection library. The oligonucleotides of the selection library (about $10^5$ oligos) contained a random region of 40 nucleotides. No counter-selection was performed. One indication that a selection was successful is the observation that the copy number of certain sequences increase over selection rounds. We analyzed a total of 6,559,573 sequences. The top twenty sequences in terms of copy number are listed below in Table 1 and referred herein as SEQ ID NOs: 3-23.

TABLE 1

| SEQ ID | Name | Sequence | Copy number | Frequency |
|---|---|---|---|---|
| 3 | Chol-1 | TAGAGAAGGCAAGAAAAAGTGAAAGAGAAGTGAACCGAGT | 4022 | 6.13E-04 |
| 4 | Chol-2 | AAACAGGTAAGATAAAGGTAGTGAGTACCAGGACGCAAGG | 3221 | 3221E-04 |
| 5 | Chol-3 | GATTCGATCTGGATAAAGTGGAGTGACTGTGTATGTGTGA | 2729 | 2729E-04 |
| 6 | Chol-4 | CAAAACTAACGAATCACGATGCGCTCTGCGTAGTCTGAGC | 2151 | 3.28E-04 |
| 7 | Chol-5 | TAGTTCGAGTAAACGAGCCAAGAGCTAAATAGCAAATGAA | 1776 | 2.71E-04 |
| 8 | Chol-6 | TGAAGATAAAAAGCCCATAAACAACTATTGGTACGAGATC | 1760 | 2.68E-04 |
| 9 | Chol-7 | ACGGGATAATTAACTAGACAGTATCACGTTTGGCTATTAG | 1741 | 2.65E-04 |
| 10 | Chol-8 | AGTCAATCACTTCACTTACGTGGTTATCTGTTTGATAAGC | 1727 | 2.63E-04 |
| 11 | Chol-9 | AAACAAGAGGACATCGTGACAAACGATATAAATGTGATTG | 1694 | 2.58E-04 |
| 12 | Chol-10 | AAGTCGTATGTCTAAAACAAGACTGTAATGCACCTCATCT | 1678 | 2.56E-04 |
| 13 | Chol-11 | GATGGGTACAAGCAAGGCAGGCCAGTTCTATTAAAGTGTG | 1676 | 2.56E-04 |
| 14 | Chol-12 | AAGAGGATAAAAACGGCTGAGCTTGGCAGTCACATATGAA | 1651 | 2.52E-04 |
| 15 | Chol-13 | GTAGACCACCGCACGACCGCTGATGCTCTTTGGCTGTCGA | 1645 | 2.51E-04 |
| 16 | Chol-14 | TAATGGCGTACACGCCTACGACACCAAAACTTCACTTTTG | 1616 | 2.46E-04 |
| 17 | Chol-15 | TTGAAAAGAAGATGGACGGTTAAGTGTAGACCTGGAATAT | 1565 | 2.39E-04 |
| 18 | Chol-16 | TGGAATCAAATGGCTCTCGCCCGACACAAGTGAATGCCAT | 1537 | 2.34E-04 |
| 19 | Chol-17 | CTAAGGTTGAAATAATAAGCGGTCAGATAAAGTGAGGGTA | 1537 | 2.34E-04 |
| 20 | Chol-18 | ATAGAAGACGTTCGACGTATGTTAACAGGGGGAAGGAAAG | 1507 | 2.30E-04 |
| 21 | Chol-19 | CTATGACTTATTATTGGGAGTAGGAATGAGCTACATTACC | 1459 | 2.22E-04 |
| 22 | Chol-20 | ACATAAAAAAGAGATGCGTGTAATGGAGACATAAAACCAA | 1432 | 2.18E-04 |
| 23 | Chol-21 | GGATCAAGGGAAAGGACAAGTAGACCTAAGCGTTTGAAAT | 1387 | 2.11E-04 |

Sequences are listed as random region only in a 5' to 3' direction.

Identified sequences (SEQ ID NOs: 3-23, Table 1) were tested for binding using a gold nanoparticle (GNP) binding assay. This protocol uses GNPs aggregation to create an amplified signal of the binding event between the aptamer and the target. Naked GNPs will aggregate in the presence of salts. GNPs that are coated with aptamer will not aggregate. The presence of a target that the GNPs bind to will modulate the ability of the DNA to adhere to the surface of the GNPs. This modulation is detected through quantitative differences in the proportion of GNPs that aggregate.

Candidate aptamers were tested with 12.5 pmoles of aptamer, incubated with gold nanoparticles and varying concentrations of 24(S) cholesterol as a target. Absorbance was measured at 520 and 620 nm. Then, 4 M NaCl was added to the mixtures to stimulate aggregation. These were allowed to incubate overnight, and the 520 and 620 nm absorbances were measured again.

Figure 2:
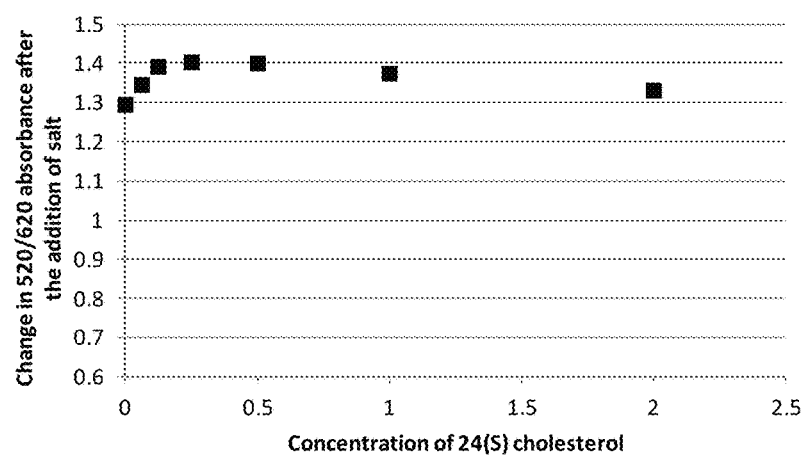
FIG. 2 is a graph, showing binding assays for aptamer chol-4 (SEQ ID NO: 6) and 24(S) cholesterol.

Both initial (i.e., before salt addition) and final (i.e., after overnight incubation) 520/620 ratios were determined, and the final 520/620 ratio was subtracted from the initial 520/620 ratio. The result obtained for aptamer chol-4 (SEQ ID NO: 6) binding to increasing concentrations of 24(S) cholesterol is plotted in FIG. 2.

The coefficient of disassociation between the aptamer and 24(S) cholesterol was determined through the use of the following equation;

$$([A_0]+[T_0]+k_D)-(([A_0]+[T_0]+k_D)^2-4[A_0][T_0])^{1/2}/2[T_0]$$

where:

$[A_0]$ and $[T_0]$ represent the concentrations of aptamer and target initially, and $k_D$ equals the coefficient of disassociation.

The invention claimed is:

1. A method for the selection of aptamers that comprises the following steps:
   a) combining a library of oligonucleotides that contain a random region flanked by two primer recognition sites (selection library) with blocker oligonucleotides (blockers) that anneal to the primer recognition sites to obtain a blocked selection library;
   b) exposing the blocked selection library to an immobilization field comprising immobilized oligonucleotides, wherein binding occurs in the random region of the oligonucleotides of said blocked selection library;
   c) removing sequences from the blocked selection library that are not bound to the immobilization field;
   d) recovering blocked selection library that were bound to the immobilization field;
   e) combining and incubating these recovered blocked selection library sequences with a target analyte;
   f) exposing the mixture of step e) with an immobilization field as in step b);
   g) retaining those blocked selection library sequences that do not bind to the immobilization field;
   h) exposing the retained blocked selection library sequences to PCR amplification;

i) repeating steps a) to h) to achieve the level of selection desired.

2. The method according to claim 1, wherein the blocked selection library is incubated with a counter-selection target analyte or complex of analytes prior to the first exposure of step b).

3. The method according to claim 1, wherein the target analyte is metabolites, toxins, proteins, peptides, cell wall or cell membrane constituents, living or dead tissue and/or complexes among any of these individual elements either as pairs or in more multitudinous combinations.

4. The method according to claim 1, wherein the target analyte is a complex formed between molecules.

5. The method according to claim 1, wherein the target analyte is either known or unknown but is present within a pre-existing complex mixture.

6. The method according to claim 5, wherein the target analyte within a pre-existing complex mixture is a complex formed between molecules.

7. The method according to claim 2, wherein the target analyte is either known or unknown but is present within a pre-existing complex mixture and where a pre-existing complex mixture is used as a counter-selection target analyte.

8. The method according to claim 7, wherein the target analyte within a pre-existing complex mixture used as a counter-selection target analyte is a complex formed between molecules.

9. The method according to claim 1, wherein the oligonucleotide is composed solely of or is a combination of any one of natural DNA nucleotides, natural RNA nucleotides, modified DNA nucleotides and modified RNA nucleotides.

10. The method according to claim 1, wherein the oligonucleotides within the immobilization field have a length of 8 nucleotides.

11. The method according to claim 1, wherein the oligonucleotides within the immobilization field have a length of 9 or 10 nucleotides at a later stage in later selection rounds, to increase the stringency of selection.

12. The method according to claim 1, wherein stringency of selection is increased by applying two positive selections.

* * * * *